(12) United States Patent
Breil et al.

(10) Patent No.: US 7,856,897 B2
(45) Date of Patent: Dec. 28, 2010

(54) APPARATUS AND METHOD FOR TAKING LIQUID SAMPLES

(76) Inventors: James J. Breil, 724 W. Massachusetts St., Hernando, FL (US) 34442; Alice J. Warren, 3634 N. Lucille Dr., Beverly Hills, FL (US) 34465

( * ) Notice: Subject to any disclaimer, the term of this patent is extended or adjusted under 35 U.S.C. 154(b) by 446 days.

(21) Appl. No.: 12/126,775

(22) Filed: May 23, 2008

(65) Prior Publication Data

US 2009/0288503 A1    Nov. 26, 2009

(51) Int. Cl.
*G01N 1/12* (2006.01)
(52) U.S. Cl. .................. 73/864.63; 73/863
(58) Field of Classification Search .......... 73/863, 73/864.63
See application file for complete search history.

(56) References Cited

U.S. PATENT DOCUMENTS

| | | | | |
|---|---|---|---|---|
| 2,177,477 A | * | 10/1939 | Dahlstrom | 73/864.63 |
| 4,515,023 A | | 5/1985 | Kershner | |
| 5,265,840 A | * | 11/1993 | Gillespie et al. | 251/4 |
| 5,465,894 A | * | 11/1995 | Clark et al. | 227/175.1 |
| 5,580,067 A | * | 12/1996 | Hamblin et al. | 227/176.1 |

* cited by examiner

*Primary Examiner*—Hezron Williams
*Assistant Examiner*—Rodney T Frank
(74) *Attorney, Agent, or Firm*—Larson & Larson, P.A.; Frank Liebenow

(57) ABSTRACT

An application for a liquid sampling device includes an elongated shaft with a handle at a first end of the elongated shaft and a sample container removably affixed to a distal end. A trigger is pivotally affixed to the handle and a flapper is pivotally affixed to the elongated shaft. The flapper is urged towards an opening in the sample bottle, thereby covering the opening in the sample container in a default position and the trigger is linked to the flapper, wherein operation of the trigger results in opening of the flapper.

18 Claims, 5 Drawing Sheets

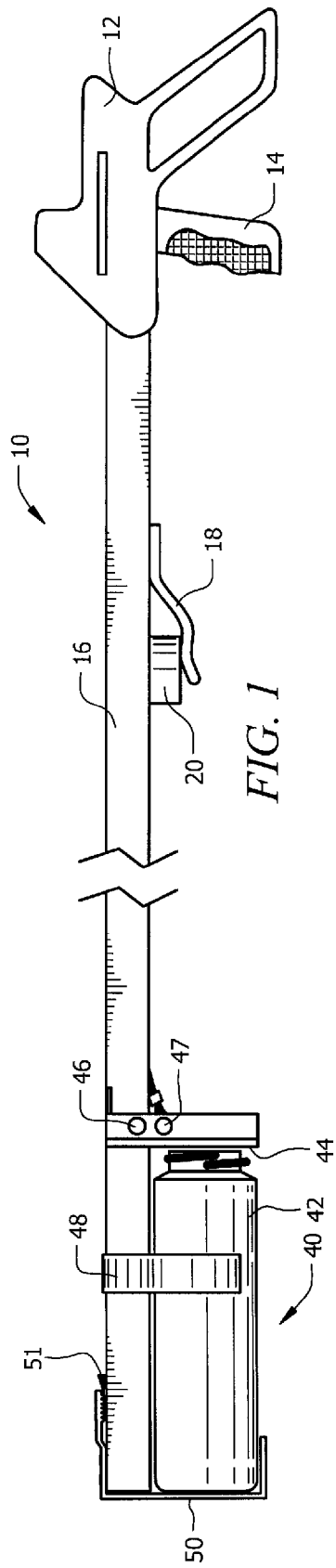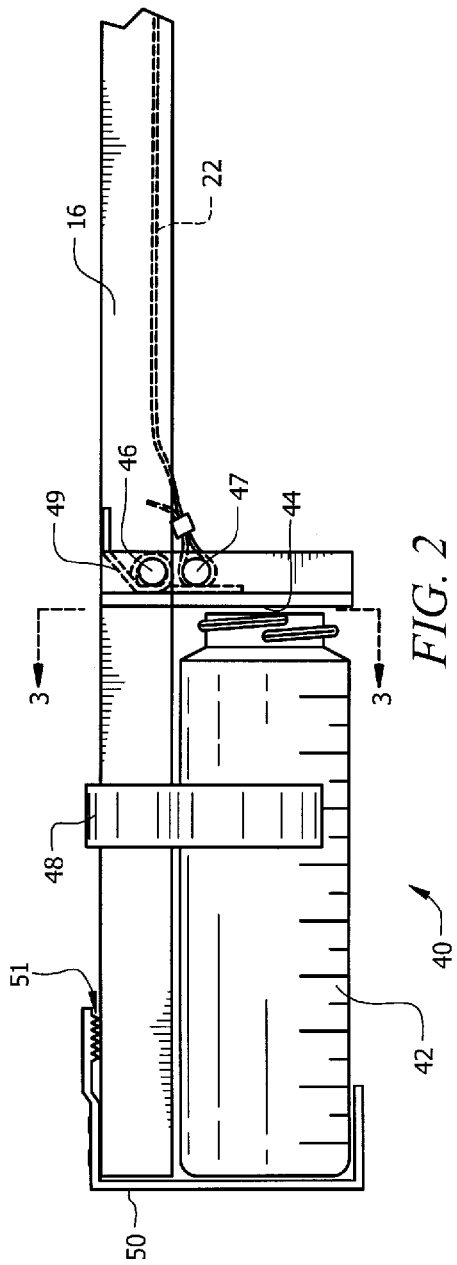

APPARATUS AND METHOD FOR TAKING LIQUID SAMPLES

FIELD OF THE INVENTION

This invention relates to the field of water sampling and more particularly to a device and method for taking a liquid sample at a desired depth beneath the surface.

BACKGROUND OF THE INVENTION

Before adding chemicals to recreational water such as that held in swimming pools and spas, it is important to test the water for residual amounts of specific chemicals such as chlorine and for other parameters such as hardness, ph, etc. In taking such samples, it is desired to take the sample at a depth at which there might be an average sample. Previously, one would hold a finger over a sample bottle, hold the sample bottle beneath the surface, remove the finger, letting water enter the sample bottle, recover the bottle with the finger, remove the bottle then test the water in the bottle. This method can test the water slightly below the surface, but not at a median level for most applications. Furthermore, the person taking the sample needs to bend down and they will get their hand and arm wet, something that is not pleasant when wearing long sleeve shirts, etc.

Likewise, water samples are often taken in streams, rivers and lakes where it is also desirable to sample at a specific depth. In such environments, it is sometimes dangerous to insert one's hand and arm into the water to take such samples due to wildlife present in the water body (e.g., alligators, snakes, leaches and sharks).

U.S. Pat. No. 4,515,023 to Kershner has a recreational pool implement that includes a water sample device. The described device includes a pole with a cavity for accepting a sample container near an insertion end. The sample end is inserted into the pool water, thereby filling the container with pool water, and then the pole is removed from the water to test the water. This patent is hereby incorporated by reference. This patent does not disclose a remote control flapper that keeps water out of the container until the container is at the desired sample depth.

What is needed is a device that will take a liquid sample at a desired depth without requiring the user to insert a body part into the liquid.

SUMMARY OF THE INVENTION

In one embodiment, a liquid sampling device is disclosed including an elongated shaft with a handle at a first end and a sample container removably affixed to a distal end. A trigger is pivotally affixed to the handle and a flapper is pivotally affixed to the elongated shaft. The flapper is urged towards an opening in the sample bottle, thereby covering the opening in the sample container in a default position and the trigger is linked to the flapper, wherein operation of the trigger results in opening of the flapper.

In another embodiment, a method of obtaining a liquid sample is disclosed including providing a liquid sampling device having an elongated shaft with a handle at a first end and a sample container removably affixed to a distal end. A trigger is pivotally affixed to the handle and a flapper is pivotally affixed to the elongated shaft and urged towards an opening in the sample bottle, thereby covering the opening in the sample container. A linkage between the trigger and the flapper provides remote control of the flapper and operation of the trigger results in opening of the flapper. The method continues with inserting the distal end of the liquid sampling device to a desired depth into the liquid then squeezing the trigger, thereby opening the flapper and allowing the liquid to enter the sample container. The trigger is then released, thereby sealing the sample container and the distal end of the liquid sampling device is removed from the liquid whereas the liquid in the sample container is available for testing.

In another embodiment, a liquid sampling device is disclosed including an elongated shaft with a handle at a first end and a sample container removably affixed to a distal end. A device for selectively sealing the sample container is affixed to the elongated shaft is urged towards an opening in the sample bottle, thereby covering the opening in the sample container until a device for remotely opening the device for selectively sealing the sample container is operated. The device for remotely opening the device for selectively sealing the sample container is affixed to the handle and is linked to the device for selectively sealing the sample container.

BRIEF DESCRIPTION OF THE DRAWINGS

The invention can be best understood by those having ordinary skill in the art by reference to the following detailed description when considered in conjunction with the accompanying drawings in which:

FIG. 1 illustrates a plan view of a system of the present invention.

FIG. 2 illustrates a close-up plan view of the remote container of the present invention.

DETAILED DESCRIPTION OF THE INVENTION

Figure 3:
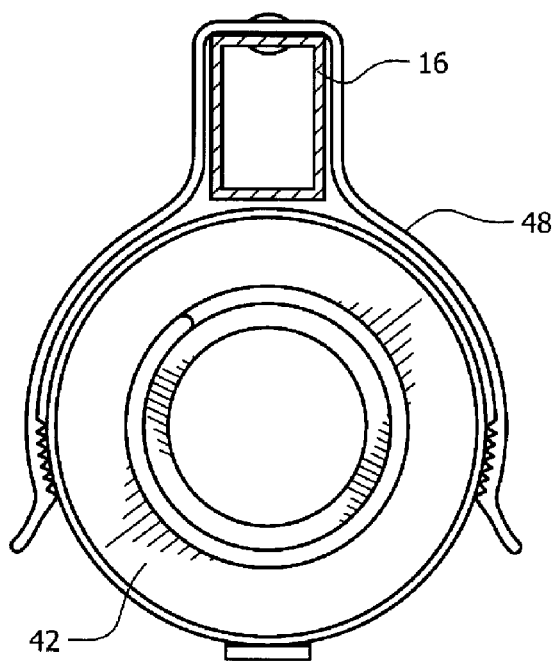
FIG. 3 illustrates a cross-sectional view of the present invention.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a plan view of a system of the present invention is shown. The remote water sampling device 10 includes an elongated shaft 16 having a handle end and a sample end. At the handle end is a handle 12 and a trigger 14. At the sample end is a remote controlled sample container 40 that is opened to take a sample remotely by the trigger 14. The remote controlled sample container 40 has a container portion 42 that is held to the elongated shaft 16 by a retainer 48 and an end cap 50. There are many known sizes and shapes of containers, many of which are equally applicable to the present invention, along with many alternative methods of holding the containers to the elongated shaft.

In the exemplary remote controlled sample container 40, a flapper 44 covers the container 42 and is hingedly affixed to the elongated shaft 16 by a hinge pin 46 or other hinge device. In this embodiment, a flexible shaft (not visible) passes within the elongated shaft 16 and couples with the flapper 44 at one end through a pin 47. The opposing end of the flexible shaft interfaces with the trigger 14 (as will be shown) to permit remote open/close operations of the flapper 44. In some embodiments, the flapper is not coated and provides a simple seal whereby air pressure prevents water leakage until the flapper 44 is opened. In some embodiments, the flapper 44 is coated with a resilient material 41 (See FIG. 8) such as soft rubber to provide a better water seal. In some embodiments, marks or gradients are printed or engraved on an outside surface of the elongated shaft providing a way to know the depth of the sample container 42 before the trigger 14 is pulled to accept the sample.

In some embodiments, an auxiliary lid 20 is held to the elongated shaft 16 by a spring clip 18. The auxiliary lid 20 is used to seal the sample container 42 when the sample container 42 is removed from the retainer 48 and end cap 50.

Referring to FIG. 2, a close-up plan view of the remote container of the present invention is shown. In this the remote controlled sample container 40 is shown in detail, held to the elongated shaft 16 by the retainer 48 and end cap 50. The flapper 44 is coupled to the elongated shaft 16 by a hinge 46 (or other hinged mechanism) and is urged closed by a spring 49. Although a torsion spring 49 is shown, any suitable spring is anticipated. The flapper 44 is coupled to the trigger 14 by a flexible shaft 22 that links to the flapper 44 by a pin 47 or other attachment mechanism as known in the industry. The flapper 44 rotates to an open position under tension of the flexible shaft 22 and restores to the closed position by force of the spring 49 when the tension of the flexible shaft 22 abates. In the example shown, the flexible shaft 22 passes through a hollow portion of the elongated shaft 16; while in other embodiments, the flexible shaft 22 passes outside the elongated shaft 16. In some embodiments, a rigid shaft (not shown) interfaces the trigger 14 with the flapper 44.

Referring to FIG. 3, a cross-sectional view of the remote controlled sample container along line 3-3 of FIG. 2 of the present invention is shown. The container portion 42 is held to the elongated shaft 16 by retainer 48.

Figure 4:
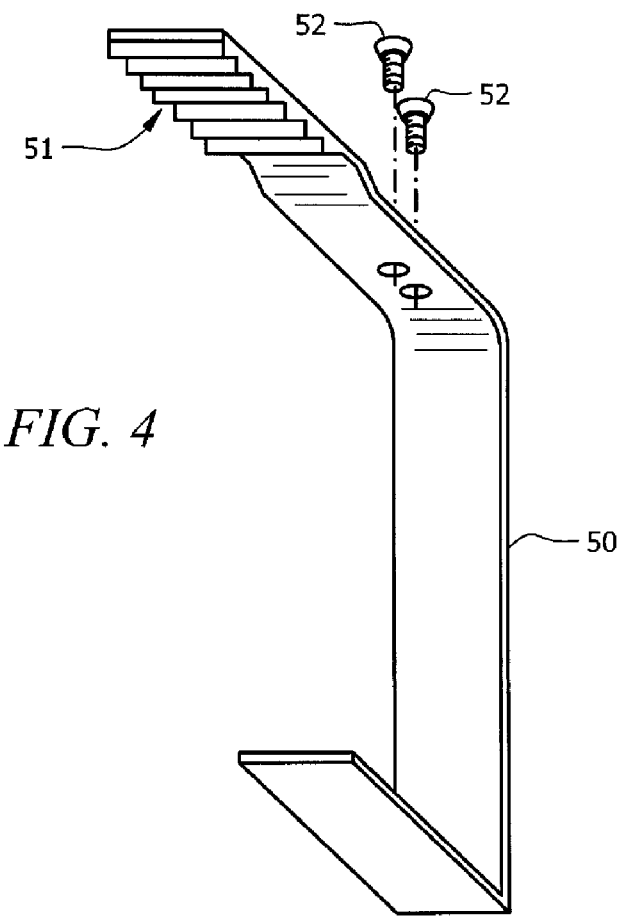
FIG. 4 illustrates a perspective view of a retainer of the present invention.

Referring to FIG. 4, a perspective view of the end cap of the present invention is shown. The typical end cap 50 is fastened to the elongated shaft 16 with fasteners 52 such as screws or rivets or fastened by any means known in the industry. Although not required in all embodiments, the end cap 50 holds the bottom of the container portion 42 so that the flapper 44 firmly closes against the lip of the container portion 42.

Figure 5:
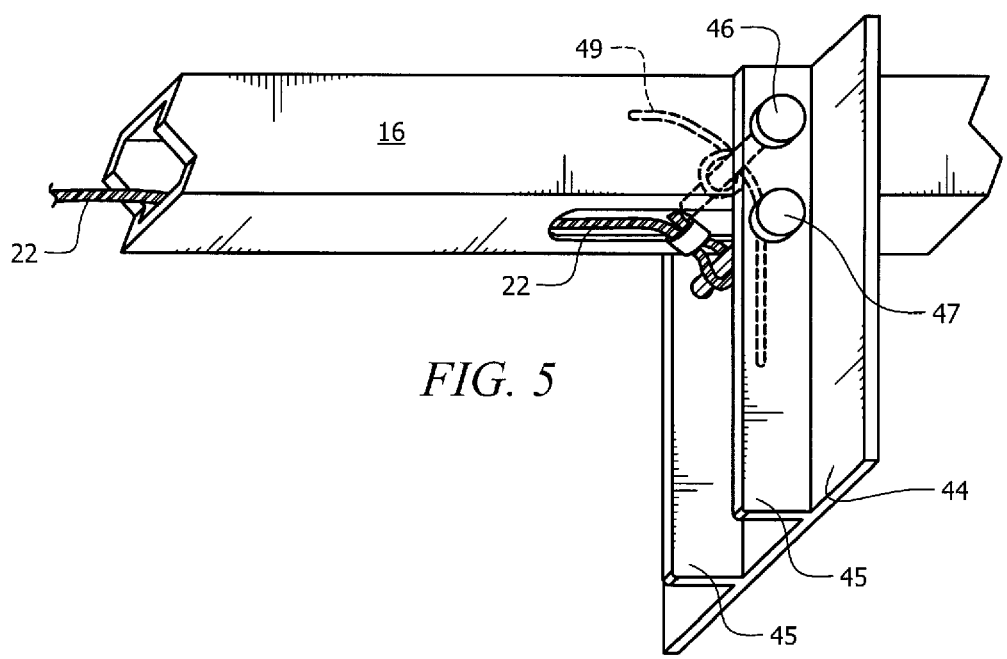
FIG. 5 illustrates a perspective detail view of the remote container cover flap of the present invention.

Referring to FIG. 5, a perspective detail view of the remote container cover flap of the present invention is shown. In this exemplary view of the remote controlled flapper 44, the flapper 44 interfaces with the trigger 14 by a flexible shaft (or wire) 22 that connects to the flapper 44 by a pin 47 or other means as known in the industry. The flapper 44 rotatably interfaces with the elongated shaft 16 by a hinge pin 46 or any other known hinge device as known in the industry. In this embodiment, a torsion spring 49 pushes against the outer wall of the elongated shaft 16 and against the flapper 44, thereby urging the flapper 44 towards the container portion 42 until the flapper 44 is pulled into an open position by the flexible shaft 22. In some embodiments, ridges 45 are formed in the flapper 44 for holding the pin 47 and hinge pin 46.

Figures 6, 7, 8:
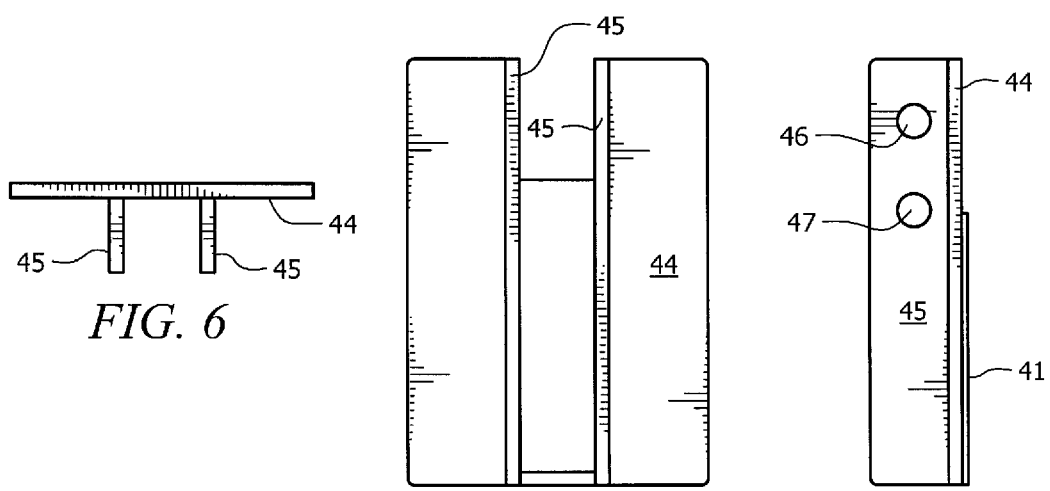
FIG. 6 illustrates a top view of the remote container cover flap of the present invention.
FIG. 7 illustrates a front view of the remote container cover flap of the present invention.
FIG. 8 illustrates a side view of the remote container cover flap of the present invention.

Referring to FIG. 6, a top view of the remote container cover flap of the present invention is shown. This view shows the flapper 44 and ridges 45 as discussed with FIG. 5.

Referring to FIG. 7, a front view of the remote container cover flap of the present invention is shown. In this view, the flapper 44 is shown with ridges 45 and a cutout area which accommodates the elongated shaft 16

Referring to FIG. 8, a side view of the remote container cover flap of the present invention is shown. The flapper 44 has holes in the ridges 45 for the hinge pin 46 and pin 47. In some embodiments, part of the surface of the flapper 44 is coated with a resilient material 41 such as rubber to provide a better water seal against the container 42. This coating of resilient material 41 covers an area at least in position where the opening of the container 42 interfaces with the flapper 44.

Figure 9:
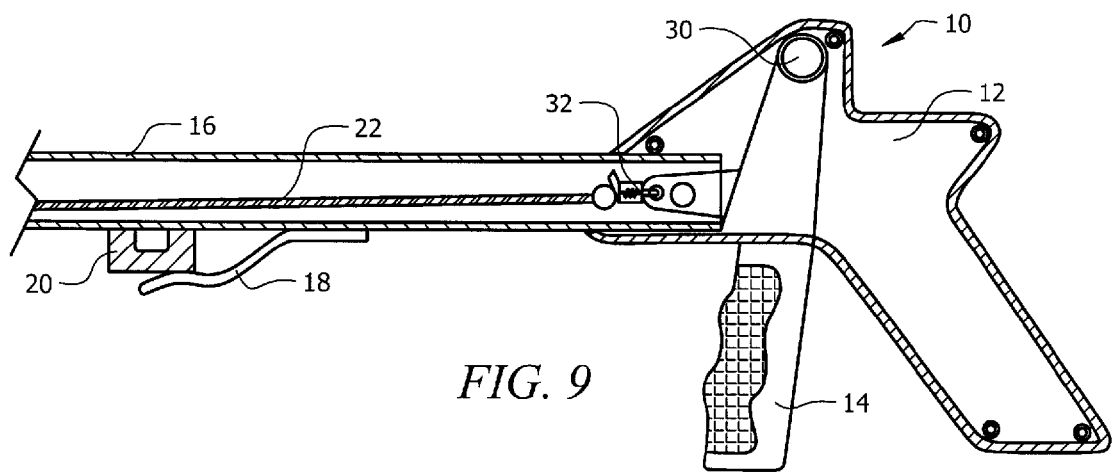
FIG. 9 illustrates a cutaway view of the apparatus of the present invention.

Referring to FIG. 9, a cutaway view of the apparatus of the present invention is shown. In this view, the trigger mechanism is visible. The trigger 14 is hingedly coupled to the handle 12 by a pivot 30 (e.g., a hinge pin). The trigger 14 is coupled to the flexible shaft 22 by a connection 32, although in other embodiments, other types of connections are anticipated as known in the industry. To open the flapper 44, the trigger 14 is pulled towards the handle 12, thereby pulling on the flexible shaft 22 and pulling the flapper 44 open.

In some embodiments, an auxiliary lid 20 is held to the elongated shaft 16 by a spring clip 18. The auxiliary lid 20 is used to seal the sample container 42 when the sample container 42 is removed from the retainer 48 and end cap 50.

Figure 10:
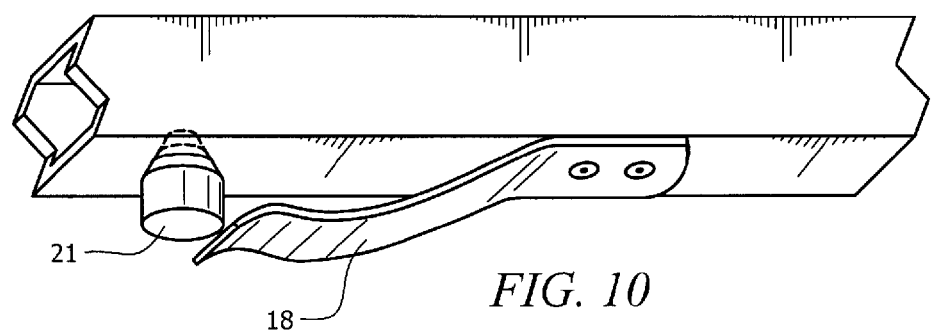
FIG. 10 illustrates a perspective view of the lid holding apparatus of the present invention.

Referring to FIG. 10, a perspective view of the lid holding apparatus of the present invention is shown. In some embodiments, an auxiliary lid 20 (not shown in FIG. 10) is held to the elongated shaft 16 by a spring clip 18. A lid retainer 21 helps hold the auxiliary lid 20 in place under the spring clip 18.

Figure 11:
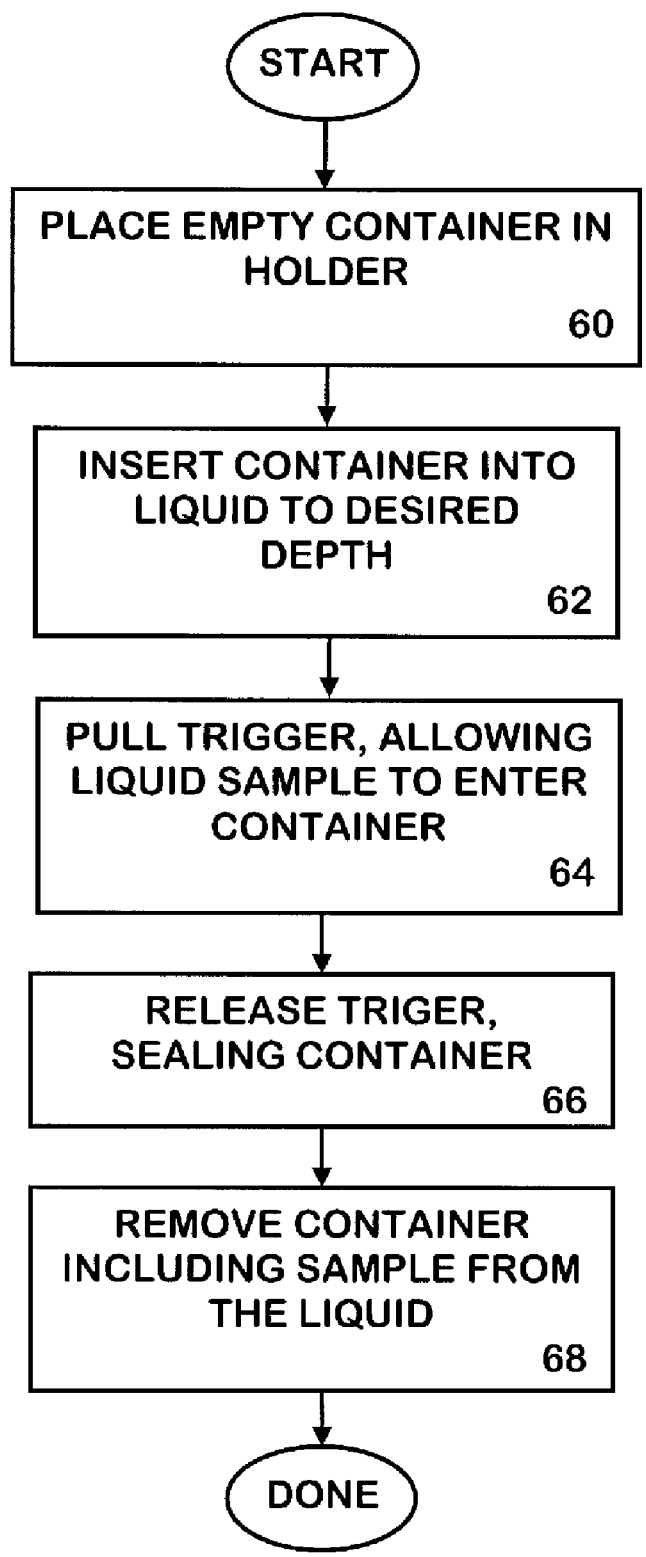
FIG. 11 illustrates a flow chart of the present invention.

Referring to FIG. 11, a flow chart of the present invention is shown. The process starts with placing an empty sample container 42 into the holder 48/50 of the present invention 60 then holding the trigger end of the water sampling apparatus and inserting the sample container 42 into the liquid to a desired depth 62. Once at the desired depth, the trigger 14 is squeezed allowing the liquid from the desired depth to enter 64 the sample container 42. The trigger is then released, thereby sealing 66 the sample container 42 and the sample container 42 is removed from the sample liquid 68, thereby allowing tests to be performed on the liquid.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A liquid sampling device comprising:

an elongated shaft;

a handle at a first end of the elongated shaft;

a trigger pivotally affixed to the handle;

a sample container removably affixed to a distal end of the elongated shaft; and a flapper pivotally affixed to the elongated shaft, the flapper urged towards an opening in the sample container, thereby covering the opening in the sample container; and a linkage between the trigger and the flapper, wherein operation of the trigger results in opening of the flapper;

wherein the flapper is urged towards the opening in the sample container by a spring.

2. The liquid sampling device of claim 1, wherein the linkage is a flexible shaft.

3. The liquid sampling device of claim 2, wherein the elongated shaft is hollow and the flexible shaft passes through the elongated shaft between the trigger and the flapper.

4. The liquid sampling device of claim 1, wherein the flapper includes a resilient layer covering at least an area of a surface of the flapper which contacts the opening in the sample container.

5. The liquid sampling device of claim 1, further comprising a spring clip affixed to the elongated shaft, the spring clip adapted to hold an auxiliary lid for the sample container.

6. The liquid sampling device of claim 5, further comprising a lid retainer affixed to the elongated shaft at a location on the elongated shaft beneath the spring clip, the lid retainer adapted to hold the auxiliary lid.

7. A method of obtaining a liquid sample comprising
providing a liquid sampling device comprising:
an elongated shaft;
a handle at a first end of the elongated shaft;
a trigger pivotally affixed to the handle;
a sample container removably affixed to a distal end of the elongated shaft; and
a flapper pivotally affixed to the elongated shaft, the flapper urged towards an opening in the sample container, thereby covering the opening in the sample container;
a linkage between the trigger and the flapper, wherein operation of the trigger results in opening of the flapper;
inserting the distal end of the elongated shaft and the sample container at a desired depth into the liquid;
squeezing the trigger, thereby opening the flapper and allowing the liquid to enter the sample container;
releasing the trigger, thereby sealing the sample container; and
removing the distal end of the elongated shaft and the sample container from the liquid whereas the liquid in the sample container is available for testing.

8. The method of claim 7, wherein the linkage is a flexible shaft.

9. The method of claim 7, wherein the elongated shaft is hollow and the flexible shaft passes through the elongated shaft between the trigger and the flapper.

10. The method of claim 9, wherein the flapper includes a resilient layer covering an area of a surface of the flapper which contacts the opening in the sample container.

11. The method of claim 7, wherein the flapper is urged towards the opening in the sample container by a spring.

12. The method of claim 7, further comprising a spring clip affixed to the elongated shaft, the spring clip adapted to hold an auxiliary lid for the sample container.

13. The method of claim 12, further comprising a lid retainer affixed to the elongated shaft at a location on the elongated shaft beneath the spring clip, the lid retainer adapted to hold the auxiliary lid.

14. The method of claim 7, wherein the elongate shaft is marked with gradients, the gradients adapted to provide a reading of the desired depth.

15. A liquid sampling device comprising:
an elongated shaft;
a handle at a first end of the elongated shaft;
a sample container removably affixed to a distal end of the elongated shaft; and
a means for selectively sealing the sample container the means for selectively sealing affixed to the elongated shaft, the means for selectively sealing urged towards an opening in the sample container, thereby selectively covering the opening in the sample container; and
a means for remotely opening the means for selectively sealing the sample container, the means for remotely opening the means for selectively sealing the sample container affixed to the handle and the means for remotely opening the means for selectively sealing the sample container is linked to the means for selectively sealing the sample container;
wherein the means for selectively sealing the sample container is urged towards the opening in the sample container by a spring.

16. The liquid sampling device of claim 15, wherein the means for remotely opening the means for selectively sealing the sample container is linked to the means for selectively sealing the sample container by a flexible shaft.

17. The liquid sampling device of claim 15, wherein the means for selectively sealing the sample container includes a resilient layer covering an area of a surface of the means for selectively sealing the sample container which contacts the opening in the sample container.

18. The liquid sampling device of claim 15, further comprising a spring clip affixed to the elongated shaft, the spring clip adapted to hold an auxiliary lid for the sample container.

* * * * *